United States Patent
Falco et al.

(12)

(10) Patent No.: US 6,548,280 B1
(45) Date of Patent: Apr. 15, 2003

(54) GENES ENCODING SULFATE ASSIMILATION PROTEINS

(75) Inventors: Saverio Carl Falco, Arden, DE (US); Stephen M. Allen, Wilmington, DE (US); Carl A. Maxwell, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/674,741

(22) PCT Filed: Jul. 13, 1999

(86) PCT No.: PCT/US99/15872

§ 371 (c)(1),
(2), (4) Date: Nov. 2, 2000

(87) PCT Pub. No.: WO00/04167

PCT Pub. Date: Jan. 27, 2000

Related U.S. Application Data

(60) Provisional application No. 60/092,833, filed on Jul. 14, 1998.

(51) Int. Cl.$^7$ .............................. C12N 9/10; C12N 1/20; C12N 15/00; C12N 15/74; C07H 21/04

(52) U.S. Cl. ................. 435/193; 435/252.3; 435/320.1; 435/471; 536/23.2; 530/350

(58) Field of Search ................................. 435/193, 471, 435/252.3, 320.1; 536/23.2; 530/350

(56) References Cited

PUBLICATIONS

EMBL Sequence Library Data Accession No: D89631, Jul. 30, 1997, Sohlberg, L.E. et al., Nucleotide Sequence of a cDNA encoding a Cys proteinase from germinating bean cotyledons, XP–0021299910.

EMBL Sequence Library Data Accession No: O49307, Jun. 01, 1998, Federspiel, N.A. et al., XP–002129911.

EMBL Sequence Library Data Accession No: D25000, Nov. 30, 1993, Minobe, Y. et al., Rice cDNA from root, XP–002129912.

Frank W. Smith et al., PNAS, vol. 92:9373–9377, Sep. 1995, Plant members of a family of sulfate transporters reveal functional subtypes, XP–002129913.

Hideki Takahashi et al., Plant & Cell Phys., vol. 39 suppl, pp. S148, 1998, Antisense repression of sulfate transporter in transgenic *Arabidopsis thaliana* plants, XP–002121793.

Hideki Takahashi et al., PNAS, vol. 94:11102–11197, Sep. 1997, Regulation of sulfur assimilation in higher plants: A sulfate trnasporter induced in sulfate–starved roots plays a central role in *Arabidopsis thaliana*.

EMBL Sequence Library Data Accession No: X96761, Mar. 25, 1997, NG, A. et al., Isolation & characterization of a lowly expressed cDNA from the resurrection grass *Sporobolus stapfianus* with homology to eukaryote sulfate transporter proteins, XP–002121791.

EMBL Sequence Library Data Accession No: AF016306, Jan. 08, 1998, Bolchi, A. et al., Coordinate modulation of maize sulfate permease and ATP sulfate permease and ATP sulfurylase mRNAs in response to variations in sulfur nutritional status: stereospecific down–regulation by L–cysteine, XP–002121790.

EMBL Sequence Data Library Accession No: O48889, Jun. 01, 1998, Bolchi, A. et al.

Frank W. Smith et al., The Plant Journal, vol. 12(4):875–884, 1997, Regulation of expression of a cDNA from barley roots encoding a high affinity sulphate transporter, XP–002129909.

Antje Prior et al., Biochimica et Biophysica Acta, vol. 1430:25–38, 1999, Structural and kinetic properties of adenylyl sulfate reductase from *Catharanthus roseus* cell cultures.

Frank W. Smith et al., PNAS, vol. 92:9373–9377, Sep. 1995, Plant Members of a Family of Sulfate Transporters Reveal Functional Subtypes.

Angelo Bolchi et al., Plant Molecular Biology, vol. 39:527–537, 1999, Coordinate Modulation of Maize Sulfate Permease and ATP Sulfurylase mRNAs in Response to Variations in Sulfur Nutritional Status: Stereospecific Down–Regulation by L–Cysteine.

Hildegard E. Arz et al., Biochimica et Biophysica Acta, vol. 1218:447–452, 1994, A cDNA for Adenylyl Sulphate (APS)–kinase from *Arabidopsis thaliana*.

Amit Setya et al., PNAS, vol. 93:13383–13388, Nov. 1996, Sulfate Reduction in Higher Plants: Molecular Evidence for a Novel 5'–adenylylsulfate Reductase.

Keiko Yonekura–Sakakibara et al., J. Biochem., vol. 124:615–621, 1998, Molecular Characterization of Tobacco Sulfite Reductase: Enzyme Purification, Gene Cloning, and Gene Expression Analysis.

Kazuki Saito et al., J. Biol. Chem., vol. 270(27):16321–16326, 1995, Molecular Cloning and Characterization of a Plant Serine Acetyltransferase Playing a Regulatory Role in Cysteine Biosynthesis from Watermelon.

National Center For Biotechnology Information General Identifier No. 1361979, Jun. 20, 2000, Saito, K. et al., Molecular Cloning and Characterization of a Plant Serine Acetyltransferase Playing a Regulatory Role in Cysteine Biosynthesis from Watermelon.

(List continued on next page.)

*Primary Examiner*—Tekchand Saidha

(57) ABSTRACT

This invention relates to an isolated nucleic acid fragment encoding a sulfate assimilation protein. The invention also relates to the construction of a chimeric gene encoding all or a portion of the sulfate assimilation protein, in sense or antisense orientation, wherein expression of the chimeric gene results in production of altered levels of the sulfate assimilation protein in a transformed host cell.

6 Claims, 3 Drawing Sheets

PUBLICATIONS

National Center For Biotechnology Information General Identifier No. 2146774, May, 5, 2000, Howarth, J.R. et al.

National Center For Biotechnology Information General Identifier No. 1107505, Mar. 19, 1996, Hell, R. et al., A cDNA Encoding Serine Acetyltransferase from *Arabidopsis thaliana*.

Senta Heiss et al., Plant Mol. Biol., vol. 39:847–857, 1999, Cloning sulfur assimlation genes of *Brassica juncea* L.: cadmium differentially affects the expression of a putative low–affinity sulfate transporter and isoforms of ATP sulfurylase and APS reductase.

John L. Wray et al., Chemico–Biological Interactions, vol. 109:153–167, 1998, Redefining reductive sulfate assimilation in higher plants: a role for APS reductase, a new member of the thioredoxin superfamily?.

Julie Ann Bick et al., Current Opinion in Plant Biology, 1998, pp. 240–244, Plant sulfur metabolism—the reduction of sulfate to sulfite.

Julie–Ann Bick et al., PNAS, vol. 95:8404–8409, Jul. 1998, Glutareodxin function for the carboxyl–terminal domain of the plant–type 5'-adenylylsulfate reductase.

Jose F. Gutierrez–Marcos et al., PNAS, vol. 93:13377–13382, 1996, Three members of a novel small gene–family from *Arabidopsis thaliana* able to complement funtionally an *Escherichia coli* mutant defective in PAPS reductase activity encode proteins with a thioredoxin–like domain and "APS reductase" activity.

EMBL Sequence Library Data Accession No: C27405, Aug. 06, 1997, Sasaki, T. et al., Rice cDNA from callus, XP–002121812.

EMBL Sequence Library Data Accession No: AF071890, Jun. 29, 1998, Mbeguie–A–Mbeguie D. et al., Molecular cloning and partial nucleotide sequence of a sulfite reductase from apricot fruit, XP–002128211.

EMBL Sequence Library Data Accession No: D50679, Dec. 01, 1997, Ideguchi, T. et al., cDNA cloning and functional expression of ferredoxin–dependent sulfite reductase from maize in *E. coli* cells, XP–002128212.

Christine Bork et al., Gene, vol. 212:147–153, 1998, Isolation and characterization of a gene for assimiliatory sulfite reductase from *Arabidopsis thaliana*.

Andreas Bruhl et al., Biochimia et Biophysica Acta, vol. 1295:119–124, 1996, A cDNA clone from *Arabidopsis thaliana* encoding plastidic ferredoxin: sulfite reductase.

Database WPI, Derwent Publ., LTD., JP–62 455773, Mitsubishi Corp., Sep. 6, 1994, XP–002121814.

EMBL Sequence Library Data Accession No: AU068082, Jun. 07, 1999, Sasaki, T. et al., Rice cDNA from callus, XP–002128630.

EMBL Sequence Library Data Accession No: AQ688702, Jul. 02, 1999, Yu, Y. et al., A BAC Encd sequencing framework to sequence the rice genome, XP–002128631.

Saito, K., Stress Responses of Photosynthetic organisms, 1998, pp. 215–226, Molecualr Aspects of Sulfur Assimilation and Acclimiation to Sulfur Supply in Plants.

Kazuki Saito et al., Plant Phys., vol. 106:887–895, 1994, Moedulation of Cystine Biosynthesis in Chloroplasts of Transgenic Tobacco Overexpressing Cystein Synthase [O–Acetylserine(thiol)–lyase]1.

Kazuki Saito et al., Comptes Rendu De L'Academie Des Sciences, vol. 319:969–973, 1996, Molecular characterization of cysteine biosynthetic enzymes in plants.

Yoo, B. et al., Plant Phys. suppl., vol. 114:267, 1997, Regulation of recombinant soybean serine acetyltransferase by CDPK.

EMBL Sequence Library Data Accession No.: p93544, May 01, 1997, Saito, K. et al., XP–002128628.

EMBL Sequence Library Data Accession No.: C26373, Aug. 06, 1997, Sasaki, T. Rice cDNa from callus, XP–002128627.

Michael A. Roberts et al., Plant Molecular biology, vol. 30:1041–1049, 1996, Cloning and characterisation of an *Arabidopsis thaliana* cDNa clone encoding an organellar isoform of serine acetyltransferase.

Kazuki Saito et al., Journ. of Biol. Chem., vol. 270(27):16321–16326, 1995, Molecular cloning and characterization of a Plant Serine aceytltransferase playing a regulatory role in cystein biosynthesis from watermelon.

EMBL Sequence Data Library Accession No: AI637166, Apr. 27, 1999, Walbot, V., Maize ESTs from various cDNA libraries sequenced at Stanford University, XP–002123195.

Sangman Lee et al., Biochem. and Biophys. Res. Comm., vol. 247:171–175, 1998, APS Kinase from *Arabidopsis thaliana*: Genomic Organization, Expression, and Kinetic Analysis of the Recombinant Enzyme.

Ajay Jain et al., Plant Phys., vol. 105:771–772, 1994, A cDNA clone for 5'–Adenylylphosphosulfate Kinase from *Arabidopsis thaliana*.

Sandra Schiffmann et al., FEBS Lett., vol. 355:229–232, 1994, APS–solfotransferase activity is identical to higher plant APS–kinase.

Julie Ann Bick et al., Current Opinion in Plant Biology, vol. 1(3):240–244, 1998, Plant Sulfur metabolism—the reduction of sulfate to sulfite.

Hildegard E. Arz et al., Biochimica et Biophysica Acta., vol. 1218:447–452, 1994, A cDNA for adenylyl sulphate (APS)–kinase from *Arabidopsis thaliana*.

```
                              1                                                            60
SEQ ID NO:2    ------------------------------------------------------------
SEQ ID NO:4    MTA-GQLLRTEPSAQ----------------------------PQRVR-HSTPPAALQADIVPSY
SEQ ID NO:6    MP--VQELQKTSPVAQDVENVVE--------------------------------------
SEQ ID NO:8    MTA-GQPLRDDP-------------------------------QPRR-HS--PPALHPAVVPAY
SEQ ID NO:10   ------------------------------------------------------------
SEQ ID NO:12   MP---TGL-------PA--------------------------------------A--NSL
SEQ ID NO:14   ARA----------------------------------------------------------
SEQ ID NO:16   MTA-GQPLRADP-------------------------------QQRR-HS--PPALHPAVVPSY
SEQ ID NO:17   MP--VGELRFSSQS---------------------------------------S--TTV
SEQ ID NO:18   MPP-AGELRHQSPSKEKLSSVTQSDEAEA--------------------------AS--AAI
SEQ ID NO:19   MAACIDTCRTGKPQISPRDSSKHHDDESGFRYMNYFRYPDRSSFNGTQKTLHTR--PLL 61                                                           120
SEQ ID NO:2    ------------------------------------------------------------L---
SEQ ID NO:4    PPPESDGDESWVWSQIKAEARRDADAEPALASFLYATVLSHASLDRSLAFQLANKLCSST
SEQ ID NO:6    -----DAEESGVWSQIKAEARRDAESEPALASYLYSTILSHSSLAASLSFHLGNKLCSST
SEQ ID NO:8    PPPESDADESWVWSQIKAEARRDADAEPALASFLYATVLSHPSLDRSLAFHLANKLCSST
SEQ ID NO:10   VAP-------DEEGWVWGQIKAEARRDAESEPALASYLYSTILSHSSLERSLSFHLGNKLCSST
SEQ ID NO:12   --------------------------------------------------------LCSST
SEQ ID NO:14   -----------------------------------------------------------
SEQ ID NO:16   PPPESGNDESWVWSQIKAEARRDADAEPALASFLYATVLSHPSLERSLSFHLANKLCSST
SEQ ID NO:17   VESTNNDETWLWGQIKAEARRDAESEPALASYLYSTILSHSSLERSLSFHLGNKLCSST
SEQ ID NO:18   SAAAADAEAAGLWTQIKAEARRDAEAEPALASYLYSTILSHSSLERSISFHLGNKLCSST
SEQ ID NO:19   EDLDRDAEVDDVWAKIREEAKSDIAKEPIVSAYYHASIVSQRSLEAALANTLSVKLSNLN
```

FIG. 1A

```
                     121                                                                          180
SEQ ID NO:2          ------------------------------------------------------------LNYKGFLAIQAHRVA
SEQ ID NO:4          LLSTLLYELFVASLAEHPYVRAAAVADLIAARSREPG-----------------------------------
SEQ ID NO:6          LLSTLLYDLFLGVLSSDASLRAAAVADLRAAARQRDPACTSFSHCLLNYKGFLAIQAQRVA
SEQ ID NO:8          LLSTLLYDLFVASLAAHPTLRAAVVADLLAARSRDPACVGFSHCLLNYKGFLAIQAQRVA
SEQ ID NO:10         LLSTLLYDLFLASFTAHPSLRAAVVADLLAARSRDPACVGFSQCLLNFKGFLAIQAHRVS
SEQ ID NO:12         LLSTLLYDLFLNAFSSDPSLRSAAVADLRAARERDPACVSYSHCLLNYKGFLACQAHRVA
SEQ ID NO:14         ------------------------------------------------------------
SEQ ID NO:16         LLSTLLYDLFVGSLAAHPTIRAAAVADLLAVRSP----------------------------
SEQ ID NO:17         LLSTLLYDLFLNAFSTDYCLRSAVVADLQAAARERDPACVSFSHCLLNYKGFLACQAHRVA
SEQ ID NO:18         LLSTLLYDLFLNTFSSDPSLRNATVADLRAARVRDPACISFSHCLLNYKGFLAIQAHRVS
SEQ ID NO:19         LPSNTLFDLFSGVLQGNPDIVESVKLDLLAVKERDPACISYVHCFLHFKGFLACQAHRIA 181                                                                          240
SEQ ID NO:2          HVLWAQQRRPLALALQSRVADVFAVDIHPAAVVGKGILLDHATGVVIGETAVVGDNVSIL
SEQ ID NO:4          ------------------------------------------------------------
SEQ ID NO:6          HKMWSQNRKPLSLALQSRIADVFSVDIHPAARIGKGVLLDHATGVVIGETAVIGNNVSIL
SEQ ID NO:8          HVLWAQDRRALALALQSRVAEVFAVDIHPAAAIGKGVLLDHATGVVIGETAVIGDNVSIL
SEQ ID NO:10         HVLWAQQRRPLALALQSRVADVFAVDIHPAAVVGKGILLDHATGVVIGETAVVGDNVSIL
SEQ ID NO:12         HLLWRQSRRPLALALHSRIADVFAVDIHPPARIGKGILFDHATGVVRETASIGNNVSIL
SEQ ID NO:14         HKLWLQGRKVLALLIQNRVSEVFAVDIHPGAKIGRGILLDHATGLVVGETAVIGNNVSIL
SEQ ID NO:16         ------------------------------------------------------------
SEQ ID NO:17         HKLWNQSRRPLALALQSRIADVFAVDIHPAARIGKGILFDHATGVVVGETAVIGNNVSIL
SEQ ID NO:18         HKLWTQSRKPLALALHSRISDVFAVDIHPAAKIGKGILLDHATGVVVGETAVIGNNVSIL
SEQ ID NO:19         HELWTQDRKILALLIQNRVSEAFAVDFHPGAKIGTGILLDHATAIVIGETAVGNNVSIL
```

FIG. 1B

```
                  241                                                           300
SEQ ID NO:2       HHVTLGGTGKAVGDRHPKIGDGVLIGAGATILGNVKIGAGAKIGAGSVVLIDVPARSTAV
SEQ ID NO:4       ------------------------------------------------------PARASPL
SEQ ID NO:6       HHVTLGGTGKQGGDRHPKIGDGVLIGAGATILGNVRIGEGAKIGAGSLVLIDVPPWTTAV
SEQ ID NO:8       HHVTLGGTGKAVGDRHPKIGDGVLIGAGATILGNVRIGAGAKIGAGSLVLIDVPPRTTAV
SEQ ID NO:10      HHVTLGGTGKAVGDRHPKIGDGVLIGAGATILGNVKIGAGAKIGAGSVVLIDVPARNTAV
SEQ ID NO:12      HHVTLGGTGKVGGDRHPKIGDGVLIGAGATILGNVKIGEGAKVGAGSVVLIDVPPRTTAV
SEQ ID NO:14      HHVTLGGTGKASGDRHPKIGDGVLIGAGATILGNICILGNIKIGDGAKIGACSVVLKEVPPRTTAV
SEQ ID NO:16      ------------------------------------------------------------
SEQ ID NO:17      HHVTLGGTGKMCGDRHPKIGDGVLIGAGATILGNVKICEGKIGAGSVVLIDVPPRTTAV
SEQ ID NO:18      HHVTLGGTGKACGDRHPKIGDGVLIGAGATILGNVKIGAGAKVGAGSVVLIDVPCRGTAV
SEQ ID NO:19      HNVTLGGTGKQCGDRHPKIGDGVLIGAGTCILGNITIGEGAKIGAGSVVLKDVPPRTTAV 301                                            339
SEQ ID NO:2       GNPARLIGGKKAEGANEEDMPGESMDHTSFIRQWSDYTI
SEQ ID NO:4       APNTR--------------------------------G
SEQ ID NO:6       GNPARLVGGKDKPNVHA-DVPGESMDHTSFISLWSDFVI
SEQ ID NO:8       GNPARLLGGK-----KGDDMPGESMDHTSFIQQWSDYSI
SEQ ID NO:10      GNPARLIGRKNGEVEKDEDMPGESMDHTSFIRQWSDYTI
SEQ ID NO:12      GNPARLVGGKEKPS-KHEDVPGESMDHTSFISEWSDYII
SEQ ID NO:14      GNPARLVGGKDNP-IKLDKMPSFTMDHTS---WSDYVI
SEQ ID NO:16      ---------------------------WSDYVI
SEQ ID NO:17      GNPARLVGGKEKPS-QLEDIPGESMDHTSFISEWSDYII
SEQ ID NO:18      GNPARLVGGKEKPTIHDEECPGESMDHTSFISEWSDYII
SEQ ID NO:19      GNPARLLGGKDNP-KTHDKIPGLTMDQTSHISEWSDYVI
```

FIG. 1C

SEQUENCE LISTING

```
<160> NUMBER OF SEQ ID NOS: 19

<210> SEQ ID NO 1
<211> LENGTH: 815
<212> TYPE: DNA
<213> ORGANISM: Zea mays
<220> FEATURE:
<221> NAME/KEY: unsure
<222> LOCATION: (545)
<221> NAME/KEY: unsure
<222> LOCATION: (615)
<221> NAME/KEY: unsure
<222> LOCATION: (648)
<221> NAME/KEY: unsure
<222> LOCATION: (668)
<221> NAME/KEY: unsure
<222> LOCATION: (702)
<221> NAME/KEY: unsure
<222> LOCATION: (721)
<221> NAME/KEY: unsure
<222> LOCATION: (728)
<221> NAME/KEY: unsure
<222> LOCATION: (743)
<221> NAME/KEY: unsure
<222> LOCATION: (746)
<221> NAME/KEY: unsure
<222> LOCATION: (761)
<221> NAME/KEY: unsure
<222> LOCATION: (768)..(769)
<221> NAME/KEY: unsure
<222> LOCATION: (777)
<221> NAME/KEY: unsure
<222> LOCATION: (789)
<221> NAME/KEY: unsure
<222> LOCATION: (794)..(795)
<221> NAME/KEY: unsure
<222> LOCATION: (811)
<221> NAME/KEY: unsure
<222> LOCATION: (813)

<400> SEQUENCE: 1
gcctcctcaa ctacaagggc ttcctcgcca tccaggccca ccgcgtcgcg cacgtgctct      60
gggcgcagca gcgacggccc ctcgcgctcg cgctccagtc ccgcgtcgcc gacgtcttcg     120
ccgttgacat ccacccgcc gccgtcgtcg ggaagggaat cctcctcgac cacgccaccg     180
gcgtcgtcat cggtgagacg gccgtcgtcg gcgacaacgt ctccatcctc caccacgtca     240
```

-continued

| | | | | |
|---|---|---|---|---|
| ccttgggcgg | gaccgggaag | gcggtgggtg | accggcaccc | caagattggg gatggcgtgc | 300 |
| tgattggagc | aggggccacc | attcttggta | acgtgaaaat | tggtgccggg gctaagattg | 360 |
| gagccggatc | cgtggtgctg | atagatgtgc | cggcgaggag | cacggcggtt gggaaccctg | 420 |
| ccaggctgat | tggtgggaag | aaggccgagg | gtgcgaatga | ggaggacatg ccaggggagt | 480 |
| ccatggatca | cacgtccttc | atacgtcaat | ggtcggacta | caccatttga gagcggttat | 540 |
| ccaangtcta | ttgctcttct | tttgtatcac | tagtaatggt | gatgtaccaa ataccgagta | 600 |
| cttgctcttg | ttgtntgcta | tggtttgtgt | attgtactta | aaacctantg ggttatgatc | 660 |
| attgtcanct | gagtgtgcca | tgcctgaata | ctggtaaatt | cnattgatgg atggcaaatc | 720 |
| ntataaantg | gttggaattt | tcnatncttg | aaacaattct | nggaaaanna acttaancga | 780 |
| ttacttatng | accnnttttt | taaaaaaaaa | nanaa | | 815 |

<210> SEQ ID NO 2
<211> LENGTH: 175
<212> TYPE: PRT
<213> ORGANISM: Zea mays

<400> SEQUENCE: 2

Leu Leu Asn Tyr Lys Gly Phe Leu Ala Ile Gln Ala His Arg Val Ala
 1               5                  10                  15

His Val Leu Trp Ala Gln Gln Arg Arg Pro Leu Ala Leu Ala Leu Gln
            20                  25                  30

Ser Arg Val Ala Asp Val Phe Ala Val Asp Ile His Pro Ala Ala Val
        35                  40                  45

Val Gly Lys Gly Ile Leu Leu Asp His Ala Thr Gly Val Val Ile Gly
    50                  55                  60

Glu Thr Ala Val Val Gly Asp Asn Val Ser Ile Leu His His Val Thr
65                  70                  75                  80

Leu Gly Gly Thr Gly Lys Ala Val Gly Asp Arg His Pro Lys Ile Gly
                85                  90                  95

Asp Gly Val Leu Ile Gly Ala Gly Ala Thr Ile Leu Gly Asn Val Lys
            100                 105                 110

Ile Gly Ala Gly Ala Lys Ile Gly Ala Gly Ser Val Val Leu Ile Asp
        115                 120                 125

Val Pro Ala Arg Ser Thr Ala Val Gly Asn Pro Ala Arg Leu Ile Gly
    130                 135                 140

Gly Lys Lys Ala Glu Gly Ala Asn Glu Glu Asp Met Pro Gly Glu Ser
145                 150                 155                 160

Met Asp His Thr Ser Phe Ile Arg Gln Trp Ser Asp Tyr Thr Ile
                165                 170                 175

<210> SEQ ID NO 3
<211> LENGTH: 597
<212> TYPE: DNA
<213> ORGANISM: Zea mays
<220> FEATURE:
<221> NAME/KEY: unsure
<222> LOCATION: (575)
<221> NAME/KEY: unsure
<222> LOCATION: (593)

<400> SEQUENCE: 3

| | | | | |
|---|---|---|---|---|
| ggcgctgtgc | gagccacacc | gcccgcacac | cccaccggcc | ggccacatag gccccgacgg | 60 |
| cgactcgaag | atgacggccg | ggcagcttct | gcgcaccgag | ccatcagccc agccccagcg | 120 |
| ggtgcgccac | agcaccccgc | cggcggcact | ccaagcagac | atcgtgccgt cgtacccgcc | 180 |

```
gcccgagtcg acggtgacg agtcgtgggt ctggtcccag atcaaggcgg aggcgcggcg    240
cgacgcggac gcggagccgg cgctggcctc cttcctctac gcgacggtgc tgtcgcacgc    300
gtccctggac cggtccctgg ccttccaact ggccaacaag ctgtgctcct ccacgctgct    360
gtcgacgctc ctctacgaac tcttcgtggc gtcgctcgcg gagcacccgt acgtccgcgc    420
ggcggcggtg gccgacctga ttgccgcgcg gtcgcgggaa cccgggcctg cgcgggcttc    480
gccactggct cctaatacaa ggggttcttg ccgttcaagc gaaccgcttg cgcaagttct    540
gtgggccaag gcccgggccc cctggcgctg gggcncaaat tcccgccttc ccnaagg        597
```

<210> SEQ ID NO 4
<211> LENGTH: 145
<212> TYPE: PRT
<213> ORGANISM: Zea mays

<400> SEQUENCE: 4

```
Met Thr Ala Gly Gln Leu Leu Arg Thr Glu Pro Ser Ala Gln Pro Gln
  1               5                  10                  15

Arg Val Arg His Ser Thr Pro Pro Ala Ala Leu Gln Ala Asp Ile Val
             20                  25                  30

Pro Ser Tyr Pro Pro Pro Glu Ser Asp Gly Asp Glu Ser Trp Val Trp
         35                  40                  45

Ser Gln Ile Lys Ala Glu Ala Arg Arg Asp Ala Asp Ala Glu Pro Ala
     50                  55                  60

Leu Ala Ser Phe Leu Tyr Ala Thr Val Leu Ser His Ala Ser Leu Asp
 65                  70                  75                  80

Arg Ser Leu Ala Phe Gln Leu Ala Asn Lys Leu Cys Ser Ser Thr Leu
                 85                  90                  95

Leu Ser Thr Leu Leu Tyr Glu Leu Phe Val Ala Ser Leu Ala Glu His
            100                 105                 110

Pro Tyr Val Arg Ala Ala Ala Val Ala Asp Leu Ile Ala Ala Arg Ser
        115                 120                 125

Arg Glu Pro Gly Pro Ala Arg Ala Ser Pro Leu Ala Pro Asn Thr Arg
    130                 135                 140

Gly
145
```

<210> SEQ ID NO 5
<211> LENGTH: 1260
<212> TYPE: DNA
<213> ORGANISM: Impatiens balsamia

<400> SEQUENCE: 5

```
gcacgagcgg cacgaggaaa gagctgctga cgatcgaaac ttcatggtcc atggaaccgt     60
ccctcgctga tcagccgagc cgcaccatct ttcaaatcac tcactgatct tttcagtttc    120
atgttccctc tgtgactagt actagtcttc ctttcccaag cgaaaaatat gccggtccaa    180
gagcttcaga agacttctcc ggtcgcacaa gatgttgaaa acgtcgttga agatgccgag    240
gaatcaggcg tctggtctca gatcaaagcc gaggcccgca gagatgccga atcagagccg    300
gctttagcga gttatctcta ctccacaatc ctttcacact cctccctcgc tgcatctctc    360
tcgttccacc ttggaaacaa gttatgctca tccacgctcc tatccactct cctatacgat    420
ctcttcctcg gtgtcttatc ttccgacgct tcgctgcgtg cggcggcagt cgcagattta    480
cgcgccgccc gacagcggga tccggcgtgc acttcgtttt ctcactgcct tctgaactac    540
```

-continued

```
aagggtttc tggcgattca agctcagagg gtgctcaca agatgtggtc ccagaaccgg    600
aagccctttt cgctggcact ccagtctcga atcgcggatg tgttttccgt ggacattcac    660
ccggcggcac ggattggcaa gggagtgttg ttggatcacg cgacgggtgt agtgattgga    720
gagacggcag tgatagggaa caacgtttcg attctccacc atgtgacgct ggaggcacg     780 ggtaagcagg gaggtgatcg gcacccgaaa attgggacg tgttctgat cggtgcgggt     840 gcgactattt tgggtaacgt taggattggg gaaggagcga agatcggtgc aggttcgctg     900
gttttgattg acgtgcctcc atggacgacg gcggtgggaa accctgctag gttggtgggt     960
gggaaggata aacctaacgt gcacgcggat gtaccaggag aatccatgga ccacacctcc    1020
ttcatttctc tgtggtcaga ttttgtgatc tgattttatg gccgatgatc gatgaggggt    1080
tttggttggt atcatttact catactaccc cataaagaac caacctccta tcttaatttc    1140
gtagcctgga tgttgtgtaa tcctatgcaa taaacaactg acagtgtgga tccggtttat    1200
ttccgatata tatatatg tataagccaa aaaaaaaaaa aaaaaaaaa aaaaaaaaa      1260
```

<210> SEQ ID NO 6
<211> LENGTH: 294
<212> TYPE: PRT
<213> ORGANISM: Impatiens balsamia

<400> SEQUENCE: 6

```
Met Pro Val Gln Glu Leu Gln Lys Thr Ser Pro Val Ala Gln Asp Val
  1               5                  10                  15

Glu Asn Val Val Glu Asp Ala Glu Glu Ser Gly Val Trp Ser Gln Ile
             20                  25                  30

Lys Ala Glu Ala Arg Arg Asp Ala Glu Ser Glu Pro Ala Leu Ala Ser
         35                  40                  45

Tyr Leu Tyr Ser Thr Ile Leu Ser His Ser Ser Leu Ala Ala Ser Leu
     50                  55                  60

Ser Phe His Leu Gly Asn Lys Leu Cys Ser Ser Thr Leu Leu Ser Thr
 65                  70                  75                  80

Leu Leu Tyr Asp Leu Phe Leu Gly Val Leu Ser Ser Asp Ala Ser Leu
                 85                  90                  95

Arg Ala Ala Val Ala Asp Leu Arg Ala Ala Arg Gln Arg Asp Pro
            100                 105                 110

Ala Cys Thr Ser Phe Ser His Cys Leu Leu Asn Tyr Lys Gly Phe Leu
        115                 120                 125

Ala Ile Gln Ala Gln Arg Val Ala His Lys Met Trp Ser Gln Asn Arg
    130                 135                 140

Lys Pro Leu Ser Leu Ala Leu Gln Ser Arg Ile Ala Asp Val Phe Ser
145                 150                 155                 160

Val Asp Ile His Pro Ala Ala Arg Ile Gly Lys Gly Val Leu Leu Asp
                165                 170                 175

His Ala Thr Gly Val Val Ile Gly Glu Thr Ala Val Ile Gly Asn Asn
            180                 185                 190

Val Ser Ile Leu His His Val Thr Leu Gly Gly Thr Gly Lys Gln Gly
        195                 200                 205

Gly Asp Arg His Pro Lys Ile Gly Asp Gly Val Leu Ile Gly Ala Gly
    210                 215                 220

Ala Thr Ile Leu Gly Asn Val Arg Ile Gly Glu Gly Ala Lys Ile Gly
225                 230                 235                 240

Ala Gly Ser Leu Val Leu Ile Asp Val Pro Pro Trp Thr Thr Ala Val
                245                 250                 255
```

Gly Asn Pro Ala Arg Leu Val Gly Gly Lys Asp Lys Pro Asn Val His
            260                 265                 270

Ala Asp Val Pro Gly Glu Ser Met Asp His Thr Ser Phe Ile Ser Leu
        275                 280                 285

Trp Ser Asp Phe Val Ile
        290

<210> SEQ ID NO 7
<211> LENGTH: 1249
<212> TYPE: DNA
<213> ORGANISM: Oryza sativa

<400> SEQUENCE: 7

```
actgggagct ccaccgcggt ggcggccgct ctagaactag tggatccccc gggctgcagg        60
cgccgccgac cgccacatat ccacacacct cgacacgacg cgacggcga cggcgacgat       120
gactgcgggc cagcctctcc gggacgatcc ccagccacgc cggcacagcc cgccggcgct       180
ccacccggcc gtcgtgccgg cgtacccgcc cccggagtcg gacgccgacg agtcgtgggt       240
ctggtcccag atcaaggccg aggcgcgccg cgacgccgac gccgagccgg cgctcgcgtc       300
gttcctctac gccaccgtgc tctcccaccc ctccctcgac cgctcgctcg ccttccacct       360
cgccaacaag ctctgctcct ccacgctgct ctccacgctc tctacgacc tcttcgtcgc       420
ctccctcgcc gcgcaccca ccctccgcgc cgccgtcgtc gccgacctcc tcgccgcgcg       480
ctccagggac cccgcctgcg tcggcttctc ccactgcctc tcaactaca agggcttcct       540
cgccatccag gccagcgcgc tcgcgcacgt gctctgggcg caggaccgcc gcgccctcgc       600
gctcgcgctc cagtcccgcg tcgccgaggt gttcgccgtc gacatccacc ccgccgccgc       660
gatcggcaag ggcgtcctcc tcgaccacgc cacgggcgtc gtcatcggag agaccgccgt       720
catcggcgac aacgtctcca tcctccacca cgtcacgctg gcgggacag gcaaggccgt       780
gggcgaccgg caccccaaga tcggcgacgg cgtcctcatt ggcgccggcg cgacgatcct       840
cggcaatgtc aggatcggcg ccggggccaa gatcggggcc gggtcgctgg tgctcatcga       900
cgtgccgccg aggaccacgg cggtggggaa tccggcgagg ctgctcggcg ggaagaaggg       960
cgacgacatg ccgggtgaat ccatggacca cacctccttc atccagcaat ggtcggacta      1020
cagcatctga gcaggacatg gtgtatgcgc tactaaattt tctccttgtt tcgagctgtg      1080
cttgaactgg tactagtggt gttattactt aataacacta caagtaatag cacaatgtgt      1140
ttctttttg cttgtaatgg ctgtaagctt tgctccggcg agctgaaggt gaaccgtact      1200
gcacattgtc gtgctcgtct ccggacactt gtactggtgt tcactttgc                 1249
```

<210> SEQ ID NO 8
<211> LENGTH: 303
<212> TYPE: PRT
<213> ORGANISM: Oryza sativa

<400> SEQUENCE: 8

Met Thr Ala Gly Gln Pro Leu Arg Asp Asp Pro Gln Pro Arg Arg His
 1               5                  10                  15

Ser Pro Pro Ala Leu His Pro Ala Val Val Pro Ala Tyr Pro Pro Pro
            20                  25                  30

Glu Ser Asp Ala Asp Glu Ser Trp Val Trp Ser Gln Ile Lys Ala Glu
        35                  40                  45

Ala Arg Arg Asp Ala Asp Ala Glu Pro Ala Leu Ala Ser Phe Leu Tyr
    50                  55                  60

```
Ala Thr Val Leu Ser His Pro Ser Leu Asp Arg Ser Leu Ala Phe His
 65                  70                  75                  80

Leu Ala Asn Lys Leu Cys Ser Ser Thr Leu Leu Ser Thr Leu Leu Tyr
                 85                  90                  95

Asp Leu Phe Val Ala Ser Leu Ala Ala His Pro Thr Leu Arg Ala Ala
            100                 105                 110

Val Val Ala Asp Leu Leu Ala Ala Arg Ser Arg Asp Pro Ala Cys Val
        115                 120                 125

Gly Phe Ser His Cys Leu Leu Asn Tyr Lys Gly Phe Leu Ala Ile Gln
    130                 135                 140

Ala Gln Arg Val Ala His Val Leu Trp Ala Gln Asp Arg Arg Ala Leu
145                 150                 155                 160

Ala Leu Ala Leu Gln Ser Arg Val Ala Glu Val Phe Ala Val Asp Ile
                165                 170                 175

His Pro Ala Ala Ile Gly Lys Gly Val Leu Leu Asp His Ala Thr
            180                 185                 190

Gly Val Val Ile Gly Glu Thr Ala Val Ile Gly Asp Asn Val Ser Ile
        195                 200                 205

Leu His His Val Thr Leu Gly Gly Thr Gly Lys Ala Val Gly Asp Arg
210                 215                 220

His Pro Lys Ile Gly Asp Gly Val Leu Ile Gly Ala Gly Ala Thr Ile
225                 230                 235                 240

Leu Gly Asn Val Arg Ile Gly Ala Gly Ala Lys Ile Gly Ala Gly Ser
                245                 250                 255

Leu Val Leu Ile Asp Val Pro Pro Arg Thr Thr Ala Val Gly Asn Pro
            260                 265                 270

Ala Arg Leu Leu Gly Gly Lys Lys Gly Asp Asp Met Pro Gly Glu Ser
        275                 280                 285

Met Asp His Thr Ser Phe Ile Gln Gln Trp Ser Asp Tyr Ser Ile
    290                 295                 300
```

<210> SEQ ID NO 9
<211> LENGTH: 1027
<212> TYPE: DNA
<213> ORGANISM: Oryza sativa

<400> SEQUENCE: 9

```
gctctgctcc tccaccctcc tctccacgct cctctacgac ctcttcctgg cttccttcac    60
cgcgcacccc tccctccgcg ccgccgtcgt cgccgacctc ctcgccgccc gctcccgcga   120
cccggcctgc gtcggcttct cccagtgcct cctcaacttc aagggcttcc tcgccatcca   180
ggcgcaccgc gtgtcgcacg tcctctgggc gcagcagcga cgccccttg ccctcgccct    240
ccagtcccgc gtcgccgacg tcttcgccgt cgacatccac cccgcggccg tcgtcggcaa   300
gggcatcctc ctcgaccacg ccaccggcgt cgtcatcggc gagaccgccg tcgtcggcga   360
caacgtctcc atcctccacc acgttacact gggtggcaca ggcaaggctg tcggtgaccg   420
gcaccccaag attggggatg gtgttctgat ggcgccgggg cgacgattc ttggcaacgt    480
caagattgga gccgggcca agattggtgc cgggtcagtg gtgctgatag atgtgccggc    540
gaggaacacg gcggtgggga atccagccag gttgattggc aggaagaacg gtgaggttga   600
gaaggatgag gacatgcccg gggaatccat ggatcacaca tccttcattc agcagtggtc   660
ggactacacc atttgagggc gacgcgccga ggtctatttc tcttcctctc tgtataatcc   720
gtagtgttga tatgccaaaa actgatgtac ttgtcgtgct ttgggtaatc tgtactgtag   780
```

```
tgttgtatca tcagccgttt tatcagtcga atgcccatgc tcatgtactg ataactggtg    840
attgatgaaa tgatgagtca ataaaagtt gtataacttt tgattttatc atttgccaga     900
tgagtcaagc ttcaaggaca cattagattg cgattttaac tttttattgt gtaaagattc    960
catatgatgt ttctgctatt ttatatgatg caactccagg tgctaaaaaa aaaaaaaaa    1020 aaaaaaa                                                             1027
```

<210> SEQ ID NO 10
<211> LENGTH: 224
<212> TYPE: PRT
<213> ORGANISM: Oryza sativa

<400> SEQUENCE: 10

```
Leu Cys Ser Ser Thr Leu Leu Ser Thr Leu Leu Tyr Asp Leu Phe Leu
  1               5                  10                  15

Ala Ser Phe Thr Ala His Pro Ser Leu Arg Ala Val Val Ala Asp
             20                  25                  30

Leu Leu Ala Ala Arg Ser Arg Asp Pro Ala Cys Val Gly Phe Ser Gln
         35                  40                  45

Cys Leu Leu Asn Phe Lys Gly Phe Leu Ala Ile Gln Ala His Arg Val
     50                  55                  60

Ser His Val Leu Trp Ala Gln Gln Arg Arg Pro Leu Ala Leu Ala Leu
 65                  70                  75                  80

Gln Ser Arg Val Ala Asp Val Phe Ala Val Asp Ile His Pro Ala Ala
                 85                  90                  95

Val Val Gly Lys Gly Ile Leu Leu Asp His Ala Thr Gly Val Val Ile
            100                 105                 110

Gly Glu Thr Ala Val Val Gly Asp Asn Val Ser Ile Leu His His Val
        115                 120                 125

Thr Leu Gly Gly Thr Gly Lys Ala Val Gly Asp Arg His Pro Lys Ile
    130                 135                 140

Gly Asp Gly Val Leu Ile Gly Ala Gly Ala Thr Ile Leu Gly Asn Val
145                 150                 155                 160

Lys Ile Gly Ala Gly Ala Lys Ile Gly Ala Gly Ser Val Val Leu Ile
                165                 170                 175

Asp Val Pro Ala Arg Asn Thr Ala Val Gly Asn Pro Ala Arg Leu Ile
            180                 185                 190

Gly Arg Lys Asn Gly Glu Val Glu Lys Asp Glu Asp Met Pro Gly Glu
        195                 200                 205

Ser Met Asp His Thr Ser Phe Ile Arg Gln Trp Ser Asp Tyr Thr Ile
    210                 215                 220
```

<210> SEQ ID NO 11
<211> LENGTH: 1131
<212> TYPE: DNA
<213> ORGANISM: Glycine max

<400> SEQUENCE: 11

```
gcacgagctg aaccacacaa acatcaccac cgaacaatgc cgacgggggtt accggcggcg     60 aattccttag tggcgccgga cgaagagggg tgggtgtggg ggcagatcaa ggcggaggcg    120
cgccgcgacg ccgagtcgga gcctgctttg gcgagctacc tctactcgac gatcctctcg    180
cactcgtcgc tcgagcgttc tctgtctttt cacctcggaa ataagctctg ttcctccacg    240
cttctctcga cgctccttta cgacctgttc ctcaacgcct tctcctccga cccctccctc    300
```

-continued

```
cgctccgccg ccgtcgccga tctccgcgct gcccgcgaac gcgacccccgc ctgcgtctcc    360 tactcccact gcctcctcaa ttacaaaggc ttcctcgctt gccaggcgca ccgtgtggcg    420
catctgttgt ggcggcaatc acggcggcca ttggctttag cgctgcactc tcgcatcgca    480
gatgtgtttg cggtggacat tcacccgccg gcaaggattg gaagggggat tttgttcgac    540
catgccactg gggttgttgt tagggagaca gcgtcaatcg ggaacaatgt gtcgatcctg    600
caccatgtta ctctgggtgg gactggcaag gttggtggag accggcatcc taagattggg    660 gatgggggtgc ttattggtgc tggtgctacc attctgggga atattaagat tgggggaaggt    720 gcaaaggttg gtgctggttc ggtggttttta attgatgtgc caccacggac aacagcagtt    780
gggaacccgg cgaggttggt tggtgggaag gagaagccct ctaagcatga ggatgtgcct    840
ggggagtcta tggaccatac ttcctttatc tctgagtggt cagattatat catttgaatt    900
tctaaggtta atcaattaat gaatgaatac ttcaaatcaa atgctatgtg ttctgctgtt    960 ctagagttttt gtaattttat atttggattg agattttgta gagaccacac tctgcttaat   1020
tatactgtat tatgactgga aattttggca gcctgcaata tagtgacata ttgtgcaaca   1080
gattatataa agctggtttt gttggttaaa aaaaaaaaaa aaaaaaaaa a             1131
```

<210> SEQ ID NO 12
<211> LENGTH: 286
<212> TYPE: PRT
<213> ORGANISM: Glycine max

<400> SEQUENCE: 12

```
Met Pro Thr Gly Leu Pro Ala Ala Asn Ser Leu Val Ala Pro Asp Glu
 1               5                  10                  15

Glu Gly Trp Val Trp Gly Gln Ile Lys Ala Glu Ala Arg Arg Asp Ala
             20                  25                  30

Glu Ser Glu Pro Ala Leu Ala Ser Tyr Leu Tyr Ser Thr Ile Leu Ser
         35                  40                  45

His Ser Ser Leu Glu Arg Ser Leu Ser Phe His Leu Gly Asn Lys Leu
     50                  55                  60

Cys Ser Ser Thr Leu Leu Ser Thr Leu Leu Tyr Asp Leu Phe Leu Asn
 65                  70                  75                  80

Ala Phe Ser Ser Asp Pro Ser Leu Arg Ser Ala Ala Val Ala Asp Leu
                 85                  90                  95

Arg Ala Ala Arg Glu Arg Asp Pro Ala Cys Val Ser Tyr Ser His Cys
            100                 105                 110

Leu Leu Asn Tyr Lys Gly Phe Leu Ala Cys Gln Ala His Arg Val Ala
        115                 120                 125

His Leu Leu Trp Arg Gln Ser Arg Arg Pro Leu Ala Leu Ala Leu His
    130                 135                 140

Ser Arg Ile Ala Asp Val Phe Val Asp Ile His Pro Pro Ala Arg
145                 150                 155                 160

Ile Gly Lys Gly Ile Leu Phe Asp His Ala Thr Gly Val Val Arg
                165                 170                 175

Glu Thr Ala Ser Ile Gly Asn Asn Val Ser Ile Leu His His Val Thr
            180                 185                 190

Leu Gly Gly Thr Gly Lys Val Gly Gly Asp Arg His Pro Lys Ile Gly
        195                 200                 205

Asp Gly Val Leu Ile Gly Ala Gly Ala Thr Ile Leu Gly Asn Ile Lys
    210                 215                 220

Ile Gly Glu Gly Ala Lys Val Gly Ala Gly Ser Val Val Leu Ile Asp
```

-continued

```
            225                 230                 235                 240
Val Pro Pro Arg Thr Thr Ala Val Gly Asn Pro Ala Arg Leu Val Gly
                245                 250                 255
Gly Lys Glu Lys Pro Ser Lys His Glu Asp Val Pro Gly Glu Ser Met
            260                 265                 270
Asp His Thr Ser Phe Ile Ser Glu Trp Ser Asp Tyr Ile Ile
            275                 280                 285
```

<210> SEQ ID NO 13
<211> LENGTH: 722
<212> TYPE: DNA
<213> ORGANISM: Glycine max

<400> SEQUENCE: 13

```
cggcacgagc tcacaaattg tggcttcaag ggaggaaggt cttggcgctg ttgattcaga     60
ataggtgtc tgaggttttt gctgtggata ttcaccctgg tgccaaaatt ggacgtggga    120
ttttgctgga tcatgcaaca ggacttgttg tggggagac tgcagttatt gggaataatg    180
tgtcaatttt gcataatgtg acattgggag ggactggtaa ggcaagtggg gatagacacc    240
ctaagattgg tgatggggtg ttgataggtg cagggacttg tattttgggg aacattaaga    300
ttggtgatgg agctaagatt ggtgcttgtt ctgttgtgtt gaaggaagtg ccaccaagga    360
ctactgctgt tgggaacct gctaggttgg ttggagggaa ggataaccct attaaattgg    420
ataagatgcc tagttttacc atggaccata cttcatggtc tgattatgtt atatagaagc    480
taattaattg tctaacatgt tttagagttt gtgtttaggt gggaattgtt ttggttgagg    540
gggcttggtt gttgtgcaag agagaatcta agttctcctg ctgacaacag gcgtcctttt    600
gaatcatcgt gttagatttt taaagaatag ttagatgtag actttgttg ttgtaagggg    660
ccatgatgac aaccctttgt gtaaaattta tgaatatgga tatttcagct tgttatggtt    720
ac                                                                  722
```

<210> SEQ ID NO 14
<211> LENGTH: 157
<212> TYPE: PRT
<213> ORGANISM: Glycine max

<400> SEQUENCE: 14

```
Ala Arg Ala His Lys Leu Trp Leu Gln Gly Arg Lys Val Leu Ala Leu
  1               5                  10                  15
Leu Ile Gln Asn Arg Val Ser Glu Val Phe Ala Val Asp Ile His Pro
             20                  25                  30
Gly Ala Lys Ile Gly Arg Gly Ile Leu Leu Asp His Ala Thr Gly Leu
         35                  40                  45
Val Val Gly Glu Thr Ala Val Ile Gly Asn Asn Val Ser Ile Leu His
     50                  55                  60
Asn Val Thr Leu Gly Gly Thr Gly Lys Ala Ser Gly Asp Arg His Pro
 65                  70                  75                  80
Lys Ile Gly Asp Gly Val Leu Ile Gly Ala Gly Thr Cys Ile Leu Gly
                 85                  90                  95
Asn Ile Lys Ile Gly Asp Gly Ala Lys Ile Gly Ala Cys Ser Val Val
            100                 105                 110
Leu Lys Glu Val Pro Pro Arg Thr Thr Ala Val Gly Asn Pro Ala Arg
        115                 120                 125
Leu Val Gly Gly Lys Asp Asn Pro Ile Lys Leu Asp Lys Met Pro Ser
    130                 135                 140
```

Phe Thr Met Asp His Thr Ser Trp Ser Asp Tyr Val Ile
145                 150                 155

<210> SEQ ID NO 15
<211> LENGTH: 415
<212> TYPE: DNA
<213> ORGANISM: Triticum aestivum

<400> SEQUENCE: 15
cggcccagac gccatcgacg cgacgacggc gacgacgacg acgacgatga cggcgggtca      60
gcccctccgc gccgaccccc agcagcgccg ccacagcccg ccggccctcc acccgccgt      120 ggtgccgtcc tacccgcccc ggagtccgg caacgacgag tcctgggtct ggtcccagat      180
caaggccgag gcgcgccgcg acgccgacgc cgagccggcg ctcgcgtcct tcctctacgc      240
caccgtgctc tcccacccct cgctcgagcg ctccctctcc ttccacctcg ccaacaagct      300
ctgctcctcc accctcctct ccacgctcct ctacgacctc ttcgtcggct ccctcgccgc      360 gcacccacc atccgcgccg ccgccgtcgc cgacctcctc gccgtgcgct cccgg           415

<210> SEQ ID NO 16
<211> LENGTH: 123
<212> TYPE: PRT
<213> ORGANISM: Triticum aestivum

<400> SEQUENCE: 16

Met Thr Ala Gly Gln Pro Leu Arg Ala Asp Pro Gln Gln Arg Arg His
1               5                   10                  15

Ser Pro Pro Ala Leu His Pro Ala Val Val Pro Ser Tyr Pro Pro Pro
                20                  25                  30

Glu Ser Gly Asn Asp Glu Ser Trp Val Trp Ser Gln Ile Lys Ala Glu
            35                  40                  45

Ala Arg Arg Asp Ala Asp Ala Glu Pro Ala Leu Ala Ser Phe Leu Tyr
        50                  55                  60

Ala Thr Val Leu Ser His Pro Ser Leu Glu Arg Ser Leu Ser Phe His
65                  70                  75                  80

Leu Ala Asn Lys Leu Cys Ser Ser Thr Leu Leu Ser Thr Leu Leu Tyr
                85                  90                  95

Asp Leu Phe Val Gly Ser Leu Ala Ala His Pro Thr Ile Arg Ala Ala
            100                 105                 110

Ala Val Ala Asp Leu Leu Ala Val Arg Ser Arg
        115                 120

<210> SEQ ID NO 17
<211> LENGTH: 294
<212> TYPE: PRT
<213> ORGANISM: Citrullus lanatus

<400> SEQUENCE: 17

Met Pro Val Gly Glu Leu Arg Phe Ser Ser Gln Ser Ser Thr Thr Val
1               5                   10                  15

Val Glu Ser Thr Thr Asn Asn Asp Glu Thr Trp Leu Trp Gly Gln Ile
                20                  25                  30

Lys Ala Glu Ala Arg Arg Asp Ala Glu Ser Glu Pro Ala Leu Ala Ser
            35                  40                  45

Tyr Leu Tyr Ser Thr Ile Leu Ser His Ser Ser Leu Glu Arg Ser Leu
        50                  55                  60

Ser Phe His Leu Gly Asn Lys Leu Cys Ser Ser Thr Leu Leu Ser Thr

```
             65                  70                  75                  80
Leu Leu Tyr Asp Leu Phe Leu Asn Ala Phe Ser Thr Asp Tyr Cys Leu
                     85                  90                  95

Arg Ser Ala Val Val Ala Asp Leu Gln Ala Ala Arg Glu Arg Asp Pro
                100                 105                 110

Ala Cys Val Ser Phe Ser His Cys Leu Leu Asn Tyr Lys Gly Phe Leu
                115                 120                 125

Ala Cys Gln Ala His Arg Val Ala His Lys Leu Trp Asn Gln Ser Arg
            130                 135                 140

Arg Pro Leu Ala Leu Ala Leu Gln Ser Arg Ile Ala Asp Val Phe Ala
145                 150                 155                 160

Val Asp Ile His Pro Ala Ala Arg Ile Gly Lys Gly Ile Leu Phe Asp
                165                 170                 175

His Ala Thr Gly Val Val Gly Glu Thr Ala Val Ile Gly Asn Asn
                180                 185                 190

Val Ser Ile Leu His His Val Thr Leu Gly Gly Thr Gly Lys Met Cys
            195                 200                 205

Gly Asp Arg His Pro Lys Ile Gly Asp Gly Val Leu Ile Gly Ala Gly
    210                 215                 220

Ala Thr Ile Leu Gly Asn Val Lys Ile Gly Glu Gly Ala Lys Ile Gly
225                 230                 235                 240

Ala Gly Ser Val Val Leu Ile Asp Val Pro Pro Arg Thr Thr Ala Val
                245                 250                 255

Gly Asn Pro Ala Arg Leu Val Gly Gly Lys Glu Lys Pro Ser Gln Leu
            260                 265                 270

Glu Asp Ile Pro Gly Glu Ser Met Asp His Thr Ser Phe Ile Ser Glu
        275                 280                 285

Trp Ser Asp Tyr Ile Ile
    290

<210> SEQ ID NO 18
<211> LENGTH: 312
<212> TYPE: PRT
<213> ORGANISM: Arabidopsis thaliana

<400> SEQUENCE: 18

Met Pro Pro Ala Gly Glu Leu Arg His Gln Ser Pro Ser Lys Glu Lys
  1               5                  10                  15

Leu Ser Ser Val Thr Gln Ser Asp Glu Ala Glu Ala Ser Ala Ala
                 20                  25                  30

Ile Ser Ala Ala Ala Asp Ala Glu Ala Gly Leu Trp Thr Gln
            35                  40                  45

Ile Lys Ala Glu Ala Arg Arg Asp Ala Glu Ala Pro Ala Leu Ala
        50                  55                  60

Ser Tyr Leu Tyr Ser Thr Ile Leu Ser His Ser Ser Leu Glu Arg Ser
 65                  70                  75                  80

Ile Ser Phe His Leu Gly Asn Lys Leu Cys Ser Ser Thr Leu Leu Ser
                 85                  90                  95

Thr Leu Leu Tyr Asp Leu Phe Leu Asn Thr Phe Ser Ser Asp Pro Ser
                100                 105                 110

Leu Arg Asn Ala Thr Val Ala Asp Leu Arg Ala Ala Arg Val Arg Asp
            115                 120                 125

Pro Ala Cys Ile Ser Phe Ser His Cys Leu Leu Asn Tyr Lys Gly Phe
        130                 135                 140
```

Leu Ala Ile Gln Ala His Arg Val Ser His Lys Leu Trp Thr Gln Ser
145                 150                 155                 160

Arg Lys Pro Leu Ala Leu Ala Leu His Ser Arg Ile Ser Asp Val Phe
                165                 170                 175

Ala Val Asp Ile His Pro Ala Ala Lys Ile Gly Lys Gly Ile Leu Leu
            180                 185                 190

Asp His Ala Thr Gly Val Val Gly Glu Thr Ala Val Ile Gly Asn
        195                 200                 205

Asn Val Ser Ile Leu His His Val Thr Leu Gly Thr Gly Lys Ala
    210                 215                 220

Cys Gly Asp Arg His Pro Lys Ile Gly Asp Gly Cys Leu Ile Gly Ala
225                 230                 235                 240

Gly Ala Thr Ile Leu Gly Asn Val Lys Ile Gly Ala Gly Ala Lys Val
                245                 250                 255

Gly Ala Gly Ser Val Val Leu Ile Asp Val Pro Cys Arg Gly Thr Ala
            260                 265                 270

Val Gly Asn Pro Ala Arg Leu Val Gly Gly Lys Glu Lys Pro Thr Ile
        275                 280                 285

His Asp Glu Glu Cys Pro Gly Glu Ser Met Asp His Thr Ser Phe Ile
    290                 295                 300

Ser Glu Trp Ser Asp Tyr Ile Ile
305                 310

<210> SEQ ID NO 19
<211> LENGTH: 336
<212> TYPE: PRT
<213> ORGANISM: Arabidopsis thaliana

<400> SEQUENCE: 19

Met Ala Ala Cys Ile Asp Thr Cys Arg Thr Gly Lys Pro Gln Ile Ser
1               5                   10                  15

Pro Arg Asp Ser Ser Lys His His Asp Asp Glu Ser Gly Phe Arg Tyr
                20                  25                  30

Met Asn Tyr Phe Arg Tyr Pro Asp Arg Ser Ser Phe Asn Gly Thr Gln
            35                  40                  45

Thr Lys Thr Leu His Thr Arg Pro Leu Leu Glu Asp Leu Asp Arg Asp
        50                  55                  60

Ala Glu Val Asp Asp Val Trp Ala Lys Ile Arg Glu Glu Ala Lys Ser
65                  70                  75                  80

Asp Ile Ala Lys Glu Pro Ile Val Ser Ala Tyr Tyr His Ala Ser Ile
                85                  90                  95

Val Ser Gln Arg Ser Leu Glu Ala Ala Leu Ala Asn Thr Leu Ser Val
            100                 105                 110

Lys Leu Ser Asn Leu Asn Leu Pro Ser Asn Thr Leu Phe Asp Leu Phe
        115                 120                 125

Ser Gly Val Leu Gln Gly Asn Pro Asp Ile Val Glu Ser Val Lys Leu
130                 135                 140

Asp Leu Leu Ala Val Lys Glu Arg Asp Pro Ala Cys Ile Ser Tyr Val
145                 150                 155                 160

His Cys Phe Leu His Phe Lys Gly Phe Leu Ala Cys Gln Ala His Arg
                165                 170                 175

Ile Ala His Glu Leu Trp Thr Gln Asp Arg Lys Ile Leu Ala Leu Leu
            180                 185                 190

Ile Gln Asn Arg Val Ser Glu Ala Phe Ala Val Asp Phe His Pro Gly
        195                 200                 205

```
Ala Lys Ile Gly Thr Gly Ile Leu Leu Asp His Ala Thr Ala Ile Val
    210                 215                 220

Ile Gly Glu Thr Ala Val Val Gly Asn Asn Val Ser Ile Leu His Asn
225                 230                 235                 240

Val Thr Leu Gly Gly Thr Gly Lys Gln Cys Gly Asp Arg His Pro Lys
                245                 250                 255

Ile Gly Asp Gly Val Leu Ile Gly Ala Gly Thr Cys Ile Leu Gly Asn
                260                 265                 270

Ile Thr Ile Gly Glu Gly Ala Lys Ile Gly Ala Gly Ser Val Val Leu
            275                 280                 285

Lys Asp Val Pro Pro Arg Thr Thr Ala Val Gly Asn Pro Ala Arg Leu
    290                 295                 300

Leu Gly Gly Lys Asp Asn Pro Lys Thr His Asp Lys Ile Pro Gly Leu
305                 310                 315                 320

Thr Met Asp Gln Thr Ser His Ile Ser Glu Trp Ser Asp Tyr Val Ile
                325                 330                 335
```

US 6,548,280 B1

GENES ENCODING SULFATE ASSIMILATION PROTEINS

This application claims the benefit of U.S. Provisional Application No. 60/092,833, filed Jul. 14, 1998.

FIELD OF THE INVENTION

This invention is in the field of plant molecular biology. More specifically, this invention pertains to nucleic acid fragments encoding sulfate assimilation proteins in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include: High affinity sulfate transporter and low affinity sulfate transporter proteins which serve to transport sulfur from the outside environment across the cell membrane into the cell (Smith et al. (1995) PNAS92(20):9373–9377). Once sulfur is in the cell sulfate adenylyltransferase (ATP sulfurylase) (Bolchia et al. (1999) *Plant Mol. Biol.* 39(3):527–537) catalyzes the first step in assimilation, converting the inorganic sulfur into an organic form, adenosine-5' phospho-sulfate (APS). Next several enzymes further modify organic sulfur for use in the biosynthesis of cysteine and methionine. For example, adenylylsulfate kinase (APS kinase), catalyzes the conversion of APS to the biosynthetic intermediate PAPS (3'-phospho-adenosine-5' phosphosulfate) (Arz et al. (1994) *Biochim. Biophy. Acta* 1218(3):447–452). APS reductase (5' adenylyl phosphosulphate reductase) is utilized in an alternative pathway, resulting in an inorganic but cellularly bound (bound to a carrier), form of sulfur (sulfite) (Setya et al. (1996) PNAS 93(23):13383–13388). Sulfite reductase further reduces the sulfite, still attached to the carrier, to sulfide and serine O-acetyltransferase converts serine to O-acetylserine, which will serve as the backbone to which the sulfide will be transferred to from the carrier to form cysteine (Yonelcura-Sakakibara et al. (1998) *J. Biolchem.* 124(3):615–621 and Saito et al. (1995) *J. Biol. Chem.* 270(27):16321–16326).

As described each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

SUMMARY OF THE INVENTION

The instant invention relates to isolated nucleic acid fragments encoding sulfate assimilation proteins. Specifically, this invention concerns an isolated nucleic acid fragment encoding a serine O-acetyltransferase and an isolated nucleic acid fragment that is substantially similar to an isolated nucleic acid fragment encoding a serene O-acetyltransferase. In addition, this invention relates to a nucleic acid fragment that is complementary to the nucleic acid fragment encoding serine O-acetyltransferase. An additional embodiment of the instant invention pertains to a polypeptide encoding all or a substantial portion of a serine O-acetyltransferase.

In another embodiment, the instant invention relates to a chimeric gene encoding a serene O-acetyltransferase, or to a chimeric gene that comprises a nucleic acid fragment that is complementary to a nucleic acid fragment encoding a serine O-acetyltransferase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a serine O-acetyltransferase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a serine O-acetyltransferase in a transformed host cell comprising: a) transforming a host cell with a chimeric gene comprising a nucleic acid fragment encoding a serine O-acetyltransferase; and b) growing the transformed host cell under conditions that are suitable for expression of the chimeric gene wherein expression of the chimeric gene results in production of altered levels of serine O-aceryltransferase in the transformed host cell.

An addition embodiment of the instant invention concerns a method for obtaining a nucleic acid fragment encoding all or a substantial portion of an amino acid sequence encoding a serine O-acetyltransferase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A, 1B, and 1C shows a comparison of the amino acid sequences set forth in SEQ ID NOs:2, 4, 6, 8, 10, 12, 14 and 16 and the *Citrullus lanatus* and *Arabidopsis thaliana* sequences (SEQ ID NO:17, 18 (gi 2146774) and 19 (gi 1107505) respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Sulfate Assimilation Proteins

| Protein | Clone Designation | SEQ ID NO: (Nucleotide) | SEQ ID NO: (Amino Acid) |
|---|---|---|---|
| Serine O-Acetyltransferase | Contig composed of:<br>ccol.pk0007.h3<br>cen3n.pk0172.h5 | 1 | 2 |
| Serine O-Acetyltransferase | Contig composed of:<br>crln.pk0085.c5<br>csclc.pk005.p2<br>p0022.cglnf80r<br>p0022.cglnf80rb<br>p0060.corac71r | 3 | 4 |
| Serine O-Acetyltransferase | ids.pk0030.b6 | 5 | 6 |
| Serine O-Acetyltransferase | rlr24.pk0069.a11 | 7 | 8 |
| Serine O-Acetyltransferase | rlr24.pk0073.d4 | 9 | 10 |
| Serine O-Acetyltransferase | srl.pk0162.a9 | 11 | 12 |
| Serine O-Acetyltransferase | srm.pk0021.f11 | 13 | 14 |
| Serine O-Acetyltransferase | wlmk4.pk0002.h5 | 15 | 16 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No.2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art or by using computer-based sequence comparison and identification tools that employ algorithms such as BLAST (Basic Local Alignment Search Tool: Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' noncoding sequences" refer to nucleotide sequences located downstrean of a coding sequence and include polyadenylation recognition sequences and other sequences encoding regulators signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcripts is a perfect complementaty copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementary of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*: Cold Spring Harbor Laboratory Press: Cold Spring Harbor, 1989 (hereinafter "Maniatis").

Nucleic acid fragments encoding at least a portion of a several sulfate assimilation protein have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other serine O-acetyltransferase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designated and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen CDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of serine O-acetyltransferase in those cells. This enzyme is involved in sulfate assimilation and the pathway leading to cysteine biosynthesis, which in turn serves as an organic sulfur donor for multiple other pathways in the cell, including methionine biosynthesis. This enzyme and the gene(s) that encodes the protein has utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant gold peptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds and, is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sulfate assimilation protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum Genet*. 32:314–331).

The production and use of plant gene-derived probes for use in genetic mapping is described in Benatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps, see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet*. 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989)*J. Lab. Clin. Med*. 11412):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res*. 18:3671), Radiation Hybrid Mapping (Walter et al. (1997) *Nature Genetics* 7:22–28) and Happy Mapping (Dear and Cook (1989) *Nucleic Acid Res*. 17:6795–6807). For these methods the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402; Koes et al. (1995) *Proc. Natl. Acad Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen. supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various chances and modifications of the invention to adapt it to various usages and conditions.

Example 1

Composition of cDNA Libraries: Isolation and Sequencing of cDNA Clones cDNA libraries representing mRNAs from various corn, impatiens, rice, soybean and wheat tissues were prepared. The characteristics of the libraries are described below.

TABLE 2 cDNA Libraries from Corn Impatiens, Rice, Soybean and Wheat

| Library | Tissue | Clone |
| --- | --- | --- |
| ccol | Corn (*Zea mays* L.) cob of 67 day old plants grown in green house | ccol.pk0007.h3 |
| cen3n | Corn (*Zea mays* L.) endosperm stage 3 (20 days after pollenation)* | cen3n.pk0172.h5 |
| crln | Corn (*Zea mays* L.) root from 7 day seedlings grown in light | crln.pk0085.c5 |
| csclc | Corn (*Zea mays* L.) 20 day seedling (germination under cold stress) | csclc.pk005.p2 |
| ids | *Impatiens balsamina* developing seed | ids.pk0030.b6 |
| p0022 | Corn (*Zea mays* L.) green leaves treated with jasmonic acid (1 mg/ml in 0.02% Tween 20) 24 hr before collection (middle ¾ of the 3rd leaf blade and mid rib only)*** | p0022.cglnf80r p0022.cglnf80rb |
| p0060 | Corn (*Zea mays* L.) leaf about one month after planting in green house | p0060.corac71r |
| rlr24 | Rice (*Oryza sativa* L.) leaf (15 days after germination) 24 hours after infection of *Magaporthe grisea* strain 4360-R-62 (AVR2-YAMO); Resistant | rlr24.pk0069.a11 rlr24.pk0073.d4 |
| srl | Soybean (*Glycine max* L.) root library | srl.pk0162.a9 |
| srm | Soybean (*Glycine max* L:) root meristem | srm.pk0021.f11 |
| wlmk4 | Wheat (*Triticum aestivum* L.) seedlings 4 hr after inoculation w/*E. graminis* and fungicide** | wlmk4.pk0002.h5 |

*This library was normalized essentially as described in U.S. Pat. No. 5,482,845, incorporated herein by reference.
**Fungicide: Application of 6-iodo-2-propoxy-3-propyl-4(3H)-quinazolinone; synthesis and methods of using this compound are described in USSN 08/545,827, incorporated herein by reference.
***Jasmonic acid is available from Sigma Chemical Co.

cDNA libraries may be prepared by any one or many method's available. For example, the cDNAs may be introduced into plasmid vectors by first preparing the cDNA libraries in Uni-ZAP* XR vectors according to the manufacturer's protocol (Stratagene Cloning Systems. La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding sulfate assimilation proteins were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Serine O-Aceryltransferase

The BLASTX search using the EST sequences from clones listed in Table 3 revealed similarity of the polypeptides encoded by the cDNAs to serine O-acetyltransferase from Citrullus lanatus (NCBI Identifier No. gi 1361979) and Arabidopsis thaliana (NCBI Identifier No. gi 2146774 and gi 1107505). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Citrullus lanatus* and *Arabidopsis thaliana* Serine O-Acetyltransferase

| Clone | Status | BLAST pLog Score |
| --- | --- | --- |
| Contig composed of: ccol.pk0007.h3 cen3n.pk0172.h5 | Contig | 95.70 (gi 2146774) |
| Contig composed of: crln.pk0085.c5 csclc.pk005.p2 p0022.cglnf80r p0022.cglnf80rb p0060.corac71r | Contig | 34.20 (gi 1361979) |
| ids.pk0030.b6 | FIS | 133.00 (gi 1361979) |
| rlr24.pk0069.a11 | FIS | 123.00 (gi 1361979) |
| rlr24.pk0073.d4 | FIS | 102.00 (gi 2146774) |
| srl.pk0162.a9 | EST | 168.00 (gi 1361979) |
| srm.pk0021.f11 | EST | 69.70 (gi 1107505) |
| wlmk4.pk0002.h5 | FIS | 30.30 (gi 1361979) |

FIG. 1 presents an alignment of the amino acid sequences set forth in SEQ ID NOs:2, 4, 6, 8, 10, 12, 14 and 16 and the *Citrullus lanatus* and *Arabidopsis thaliana* sequences (SEQ ID NOs:17, 18 (gi 2146774) and 19 (gi 1107505) respectively). The data in Table 4 represents a calculation of the percent identity of the amino acid sequences set forth in SEQ ID NOs:2, 4, 6, 8, 10, 12, 14 and 16 and the *Citrullus*

*lanatus* and *Arabidopsis thaliana* sequences (SEQ ID NOs:17, 18 (gi 2146774) and 19 (gi 1107505) respectively).

TABLE 4

Percent Identity of Amino Acid Sequences Deduced From the Nucleotide Sequences of cDNA Clones Encoding Polypeptides Homologous to *Citrullus lanatus* and *Arabidopsis thaliana* Serine O-Acetyltransferase

| SEQ ID NO. | Percent Identity to |
| --- | --- |
| 2 | 82% (gi 2146774) |
| 4 | 45% (gi 1361979) |
| 6 | 80% (gi 1361979) |
| 8 | 72% (gi 1361979) |
| 10 | 81% (gi 2146774) |
| 12 | 87% (gi 1361979) |
| 14 | 81% (gi 1107505) |
| 16 | 52% (gi 1361979) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a serine O-acetyltransferase. These sequences represent the first corn, impatiens, rice and wheat sequences encoding serine O-acetyltransferase Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML103 has been deposited under the terms of the Budapest Treaty at ATCC (American Type Culture Collection 10801 University Blvd., Manassas, Va. 20110–2209) and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+)(Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellurn of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Pat. Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be venerated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface stertilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. 1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

What is claimed is:

1. An isolated nucleic acid fragment encoding a serine O-acetyltransferase comprising:
   (a) a nucleotide sequence encoding an amino acid sequence of at least 90% sequence identity, based on the Clustal method of alignment, when compared to one of SEQ ID NOs: 12 or 14; or
   (b) a full complement of the nucleotide sequence of (a).

2. The isolated nucleic acid fragment of claim 1 wherein the nucleic acid fragment is a functional RNA.

3. The isolated nucleic acid fragment of claim 1 wherein the nucleotide sequence of (a) comprises one of SEQ ID NOs: 11 or 13.

4. A chimeric gene comprising the isolated nucleic acid fragment of claim 1 operably linked to at least one regulatory sequence.

5. A transformed host cell comprising the chimeric gene of claim 4.

6. A method of altering the level of expression of a sulfate assimilation protein in a host cell comprising:
   (a) transforming a host cell with the chimeric gene of claim 4; and
   (b) growing the transformed host cell produced in step (a) under conditions that are suitable for expression of the chimeric gene wherein expression of the chimeric gene results in production of altered levels of the sulfate assimilation protein in the transformed host cell.

* * * * *

UNITED STATES PATENT AND TRADEMARK OFFICE
CERTIFICATE OF CORRECTION

PATENT NO.   : 6,548,280 B1
DATED        : April 15, 2003
INVENTOR(S)  : Allen Stephen M., Falco Saverio Carl and Maxwell A. Carl It is certified that error appears in the above-identified patent and that said Letters Patent is hereby corrected as shown below:

Column 2,
Line 54, delete "FIGS" and insert -- Figures --.

Column 43,
Line 36, after "claim 1" insert -- , --.

Signed and Sealed this

Twenty-first Day of September, 2004

JON W. DUDAS
*Director of the United States Patent and Trademark Office*